United States Patent
Murphy et al.

(10) Patent No.: US 7,976,515 B2
(45) Date of Patent: Jul. 12, 2011

(54) IV REGULATOR WITH INTEGRAL FLUSHING MECHANISM

(76) Inventors: Todd Murphy, Baltimore, MD (US); Christopher Klassen, Jacksonville, FL (US); Eric Schneider, Catonsville, MD (US); Brian Lee Lipford, Bel Air, MD (US)

(*) Notice: Subject to any disclaimer, the term of this patent is extended or adjusted under 35 U.S.C. 154(b) by 178 days.

(21) Appl. No.: 11/974,586

(22) Filed: Oct. 15, 2007

(65) Prior Publication Data
US 2008/0091150 A1    Apr. 17, 2008

Related U.S. Application Data

(60) Provisional application No. 60/851,856, filed on Oct. 13, 2006.

(51) Int. Cl.
*A61M 5/00* (2006.01)
*A61M 5/14* (2006.01)
(52) U.S. Cl. ........................ 604/250; 604/251
(58) Field of Classification Search ........... 604/246–256
See application file for complete search history.

(56) References Cited

U.S. PATENT DOCUMENTS

| | | | | | |
|---|---|---|---|---|---|
| 4,908,019 | A | * | 3/1990 | Urquhart et al. | 604/85 |
| 5,728,077 | A | * | 3/1998 | Williams et al. | 604/246 |
| 5,807,312 | A | * | 9/1998 | Dzwonkiewicz | 604/30 |
| 6,638,263 | B1 | * | 10/2003 | Theeuwes et al. | 604/500 |
| 7,327,273 | B2 | * | 2/2008 | Hung et al. | 340/619 |
| 2006/0122562 | A1 | * | 6/2006 | Needle et al. | 604/185 |

* cited by examiner

*Primary Examiner* — Kevin C Sirmons
*Assistant Examiner* — Imani Hayman
(74) *Attorney, Agent, or Firm* — Ober, Kaler, Grimes & Shriver; Royal W. Craig

(57) ABSTRACT

The present invention describes IV regulators that allow interruption of normal controlled-flow for a safe and convenient bolus flush, either for a specific period of time or for a specific volume of saline flush. Two time-controlled IV regulators are shown, one employing a pneumatic cylinder counter-opposed by elastic band(s) for administering a bolus flush, and one employing a compressible lever and torsion spring counter-opposed by a rotary damper. In both cases the mechanisms disengage the roller-clamp from the IV tube for a predetermined amount of time to fully open fluid flow there through for a bolus flush before return to the regulated-flow position. The volume-controlled flow regulator employs two internal bladders and allows one bladder to fill while the other bladder drains (and vice versa) by flipping a slider paddle-type toggle, thus enabling the administration of a set volume of flush fluid.

8 Claims, 11 Drawing Sheets

SECTION A-A

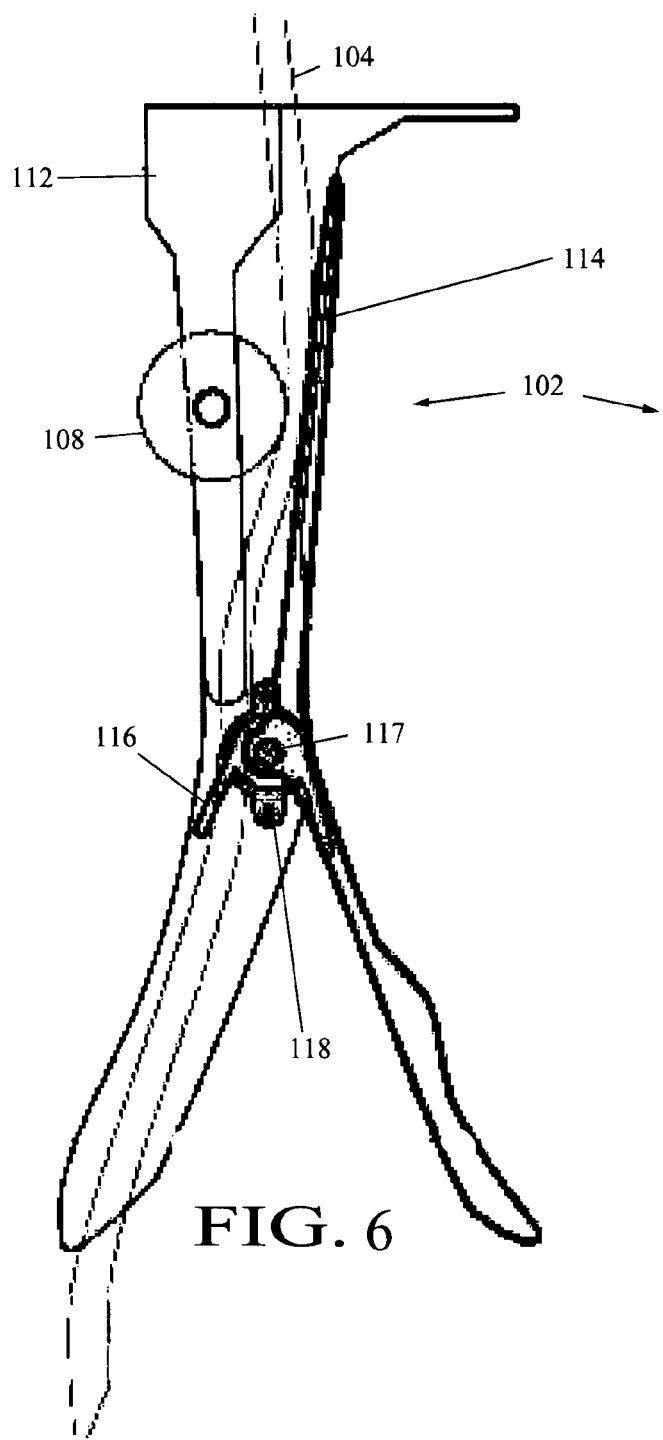
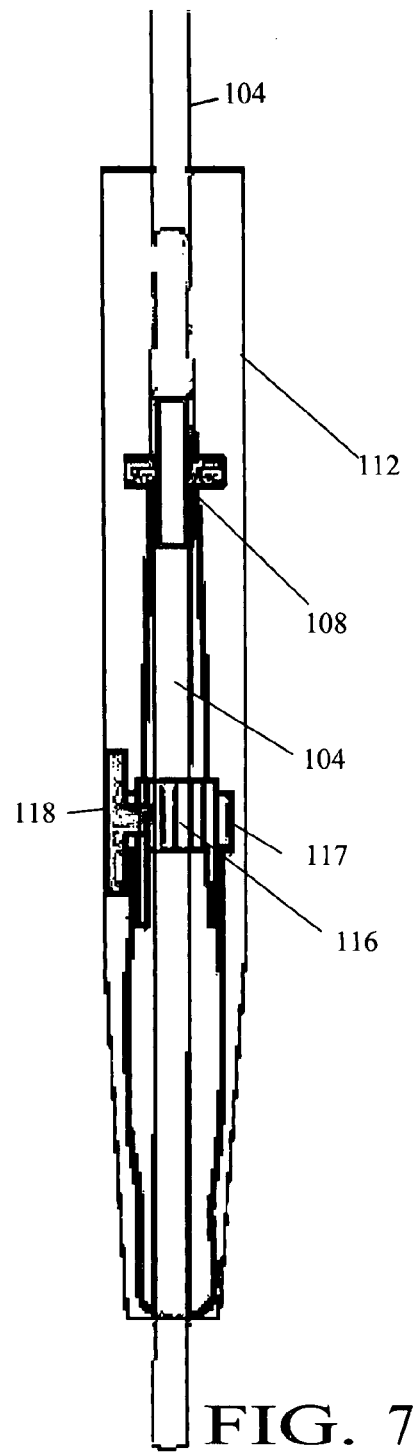
FIG. 6
FIG. 7

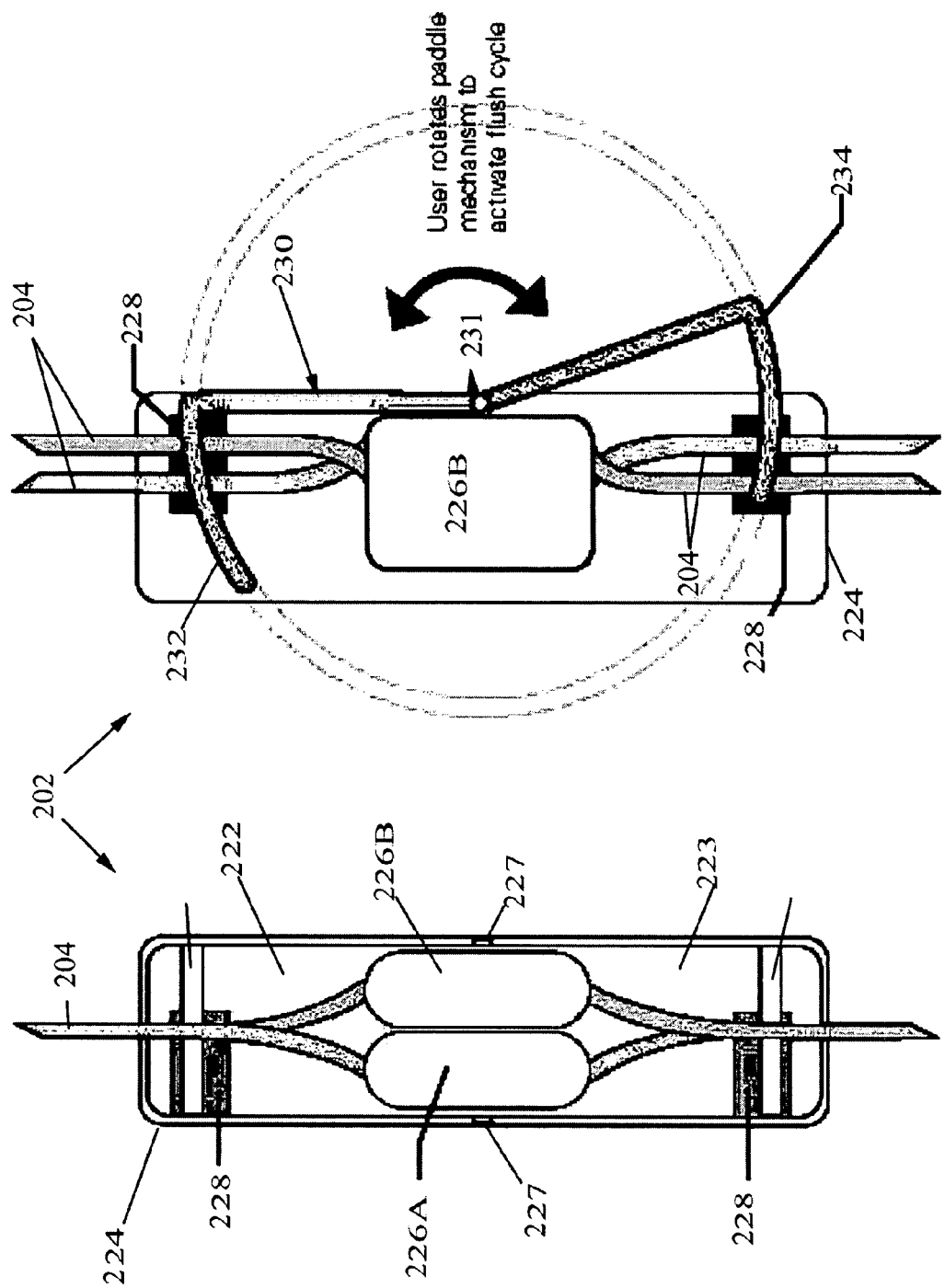

IV REGULATOR WITH INTEGRAL FLUSHING MECHANISM

CROSS-REFERENCE TO RELATED APPLICATION(S)

The present application derives priority from U.S. provisional application Ser. No. 60/851,856 filed 13 Oct. 2006.

BACKGROUND OF THE INVENTION

1. Field of the Invention

The present invention relates to flow regulators for intravenous (IV) equipment and, more particularly, to a manually-operated regulator that allows interruption of normal controlled-flow for a safe and convenient bolus flush (full flow of saline for a specific period of time or volume of flush) before returning to a "pre-flush" flow setting, eliminating the need to manually reset the roller regulator or to administer a separate saline flush.

2. Description of the Background

Intravascular or IV sets deliver fluid, medications, blood products and parenteral nutrition to patients. Most IV machines operate by gravity or by an infusion pump (a pump, usually peristaltic, used to control the flow through the IV tube). FIG. 14 is a perspective view of a conventional IV administration set, which includes an injectable solution bag, opening to a drip chamber, connected by flexible tubing to a roller-clamp and on to a catheter adapter which can be coupled to a catheter for administration to a patient. Intravenous therapy is a complex process usually requiring the preparation of machine, IV lines and medicine before administration to the patient. This involves a number of considerations, such as air or gas bubble detection, gas removal, and flow rate control. Roller-clamps as in FIG. 14 are the most widely used flow control device. The roller-clamp comprises a wheel trapped within a housing that compresses the IV tubing as it is slid along a gradual ramp. The flow rate is calculated by counting drops in a drip chamber. The infusion can be driven by gravity alone, or by an electronic infusion pump. The US market for roller-clamp-type IV administration sets is estimated at 1.4 billion dollars.

To administer a drug into a patient using an existing IV set with a roller-clamp regulator, the drug is typically injected into the IV upstream (proximal) of where it enters the patient's body. Methods of administering IV medication may include giving the medication intermittently over a specific amount of time using a secondary IV line, or giving the medication continuously mixed in the main IV solution. IV push medication techniques deliver a bolus (a dose of medication injected all at once intravenously) of medication directly into a vein or access port to produce an immediate peak drug level in the patient's bloodstream. A bolus injection is most often given through a peripheral IV line, a saline lock, or through a vascular access port. After injection, a saline "flush" is necessary to ensure delivery of the medicine to the patient's circulation. To accomplish a flush, one of two methods is typically employed. First, the user may open the roller-clamp to full flow for a brief period of time, then return it to the desired setting once the drug has been flushed into the circulation. This method leaves open the possibility that the user will forget to return the clamp to the pre-flush setting, thus causing the accidental administration of a large volume of IV fluid (an event which at best is embarrassing but innocuous, and at worst fatal). A second method of administering a flush is to draw up a separate syringe of flush solution (typically saline). The separate saline flush is administered as a "chaser" through the same port as the injected medicine. This method is fraught with its own problems ranging from wasteful use of supplies to infection control issues.

Manufacturers are approaching this problem by trying to develop computerized IV machines that can administer preprogrammed amounts of saline chasers. These devices include a twin-head injector equipped with two syringes, one for saline and one for medication. The devices can be preprogrammed to control the quantity and injection rate of both medication and saline. For example, U.S. Pat. No. 6,641,562 to Peterson (HPS Medical, Inc.) issued Nov. 4, 2003 shows an apparatus and method of intravenous fluid infusion that uses a microcomputer to cyclically drive a fluid control module which outputs a fixed amount of medicine for each cycle of operation. Unfortunately, this and like systems are far more complicated than the classic roller regulator, more expensive and difficult to use. Moreover, they do not supplant the need for the traditional manual roller-clamp regulator which is still used to regulate the flow rate at baseline.

Given the problems associated with the traditional manner of administering a saline flush, it would be much more advantageous to provide a purely mechanical (or electromechanical) device (either incorporated into or separate from the roller-clamp) capable of delivering a saline flush following a bolus of medication.

The foregoing has been attempted in one known case. U.S. Pat. No. 6,500,156 to Stansbury (McKinley Medical L.L.L.P) issued Dec. 31, 2002 shows a thumb-powered flushing device for catheters in which a chamber is covered with a flexible diaphragm that can be compressed by exertion of pressure on the diaphragm to propel fluid through the catheter, and a valve that regulates flow into and out of the chamber beneath the movable member that pumps fluid to deliver a bolus of medication, or to flush the catheter. Unfortunately, the thumb-pump action is hard to control and the amount of flush dosage delivered is at the mercy of the coordination of the user's thumb. This only marginally solves the aforesaid problem in administering a calibrated dosage of saline IV flush, and consequently has not been widely adopted.

It would be greatly advantageous to provide a simple manually-operated mechanism capable of easy integration into otherwise-conventional roller-clamp regulators that will administer an accurate flush by allowing full flow of saline for a specific period of time (or volume) before returning to a "pre-flush" setting, eliminating the need to change the setting of the roller-clamp regulator or to administer a separate saline flush injection.

SUMMARY OF THE INVENTION

It is therefore an object of the present invention to provide a purely mechanical IV flush device capable of delivering a saline flush, in a safe and convenient manner.

It is another object to provide three different embodiments of an IV flush device, two of which allow interruption of normal controlled-flow for a safe and convenient bolus flush (full flow of saline or other carrier fluid) for a specific period of time, and the third of which allows a like interruption for a specific volume of saline flush.

It is another object to provide IV devices as described above that accomplish a semi-automatic flush using components and a form factor that are as similar as possible to existing commercial roller-clamp regulators, thereby giving a familiar look and feel to doctors and nurses in order to encourage widespread adoption.

In accordance with the foregoing objects, the present invention provides three embodiments of an IV regulator: two of which allow interruption of normal controlled-flow for a safe and convenient bolus flush for a specific period of time, and the other of which allows a like interruption for a specific volume of saline flush.

One of the time-controlled IV regulators generally comprises an elongated housing seating a roller-clamp, and through which the IV tuning passes. The housing also includes a pneumatic cylinder (much like a syringe) with a pressure chamber and plunger slidably loaded into the pressure chamber. A pair of elastic bands bias the plunger upward inside the housing. To administer a bolus flush, the plunger is thumb-depressed downward and air is freely inducted into the pressure chamber (through a check valve). This disengages the roller-clamp and allows free flow for a bolus flush. When released, the plunger is biased back by the rubber bands and eventually reengages the roller clamp (after a predetermined time interval), thereby resuming controlled flow.

The second time-controlled IV regulator generally comprises a main housing section having an IV tube running through it, a roller-clamp rotatably seated in the main housing section, and a compressible handle pivotally mounted to the main housing section at a pivot pin and extending past to selectively engage the roller-clamp. A torsion spring is mounted on the pivot pin to bias the compressible lever toward a normally closed position (which engages the roller-clamp), thereby allowing adjustment of the flow rate through the IV tube. In addition, a rotary damper is engaged to the compressible lever to oppose the torsion spring bias for a predetermined amount of time, thereby allowing the compressible lever to pivotally disengage the roller-clamp from the IV tube and fully open fluid flow for a time-controlled flush before returning to the regulated flow-controlled position.

The volume-controlled flow regulator generally comprises an enclosed housing having an inlet at one end for entry of a pair of IV tubes, and an outlet at the other end for egress of a pair of IV tubes. A pair of expandable/collapsible bladders are resident in the housing, each bladder being connected endwise between two of the IV tubes. In addition, a slider paddle is pivotally mounted to the housing and is pivotable between two positions, one clamping off the tube above one bladder and opening the tube from below that bladder, thereby allowing that bladder to drain. At the same time the slider paddle opens the inlet tube to the other bladder and clamps off its outlet tube allowing it to fill. The slider paddle is pivoted to a second position reversing the fill/drain operation of the bladders. A regular IV flow can be maintained through a roller-clamp regulator either in series with (above) the present device or in parallel with it. When a medicine is then delivered into the line distally, the slider paddle can be pivoted to empty the full bladder, thereby safely administering a bolus flush of saline in a prescribed volume.

All of the foregoing embodiments allow interruption of normal regulated flow for a safe and convenient bolus flush (full flow of saline), the first two for a specific period of time, and the third for a specific volume of saline flush, before returning to a "pre-flush" normal flow setting. This simplifies the process of administering a bolus medicine followed by a saline flush. Furthermore, it improves safety, eliminates over flushing, and decreases costs associated with nursing time and supplies needed to draw up saline flush syringes.

BRIEF DESCRIPTION OF THE DRAWINGS

Other objects, features, and advantages of the present invention will become more apparent from the following detailed description of the preferred embodiment and certain modifications thereof when taken together with the accompanying drawings in which:

FIG. 6 is a side cross-section of the regulator 102 as in FIG. 5.

FIG. 7 is a front cross-section of the regulator 102 of FIGS. 5-6.

FIGS. 10 and 11 are a front cross-section and side cross-section, respectively, of an alternate embodiment of the regulator 202 that administers a calibrated volume of bolus flush before returning to a "pre-flush" flow setting.

DETAILED DESCRIPTION OF THE PREFERRED EMBODIMENTS

The present invention is a manually-operated regulator for IV tubing that allows interruption of normal controlled-flow for a safe and convenient bolus flush (full flow of saline for a specific period of time or volume of saline) before returning to a "pre-flush" flow setting, eliminating the need to manually reset the roller-clamp regulator or to administer a separate saline flush injection. Three embodiments are disclosed, two for administering a flush for a specific period of time, and one for a specific volume of flush solution.

Figure 1:
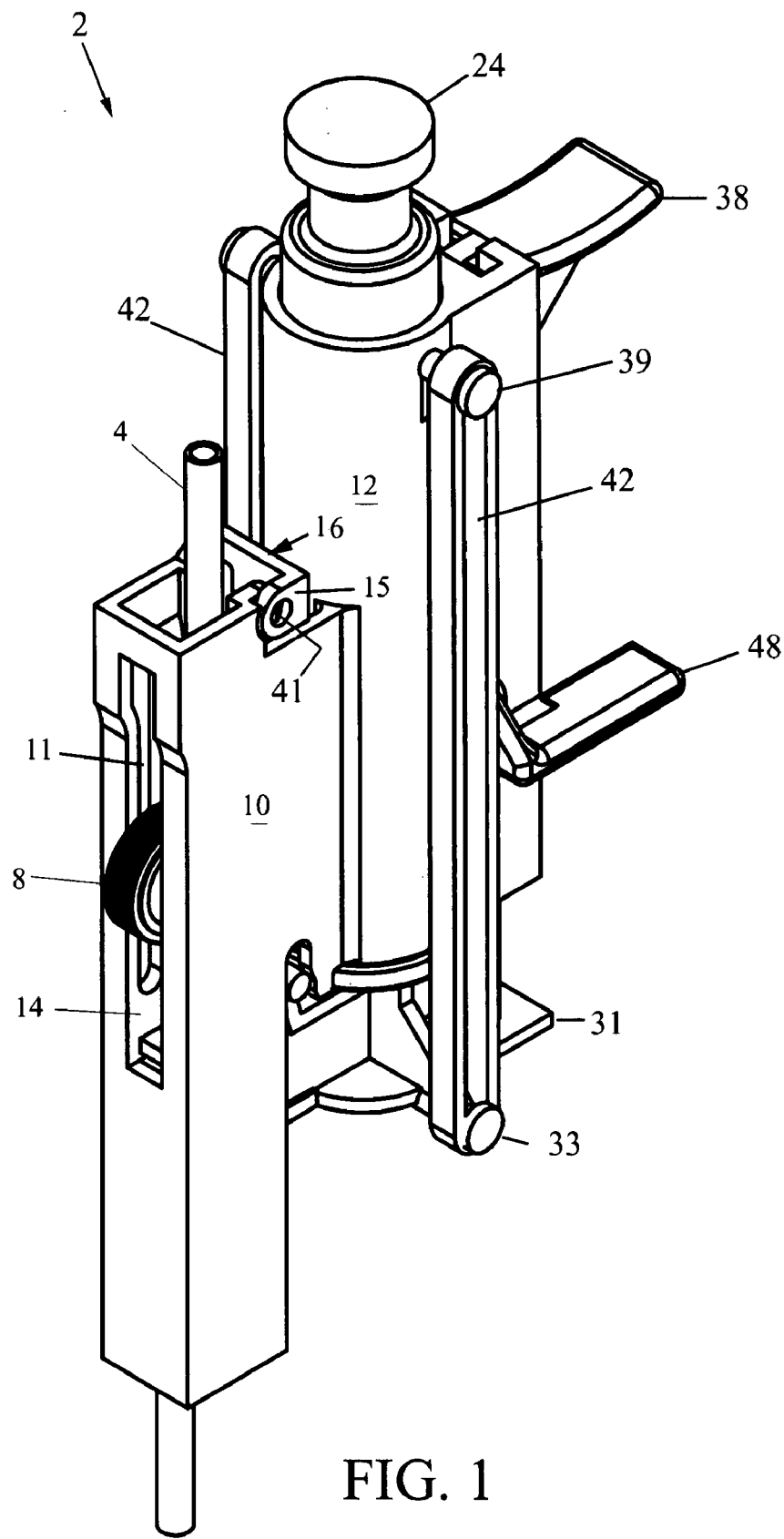
FIG. 1 is a perspective view of a regulator 2 for IV tubing according to a first embodiment that interrupts normal flow to flush for a specific period of time before returning to roller-clamp regulated flow.

FIG. 1 is a perspective view of a regulator 2 for IV tubing according to a first embodiment that interrupts normal flow to flush for a specific period of time before returning to pre-flush flow. The regulator 2 generally comprises an elongated housing with main section 10 and a plunger section 12. The main section 10 is formed as a three-walled elongate trough, and the existing IV tubing 4 runs through the trough of main section 10. A roller-clamp 8 is rotatably seated across the trough of the main section 10 and protrudes out of an aperture 14 in the front face of main section 10.

Figure 2:
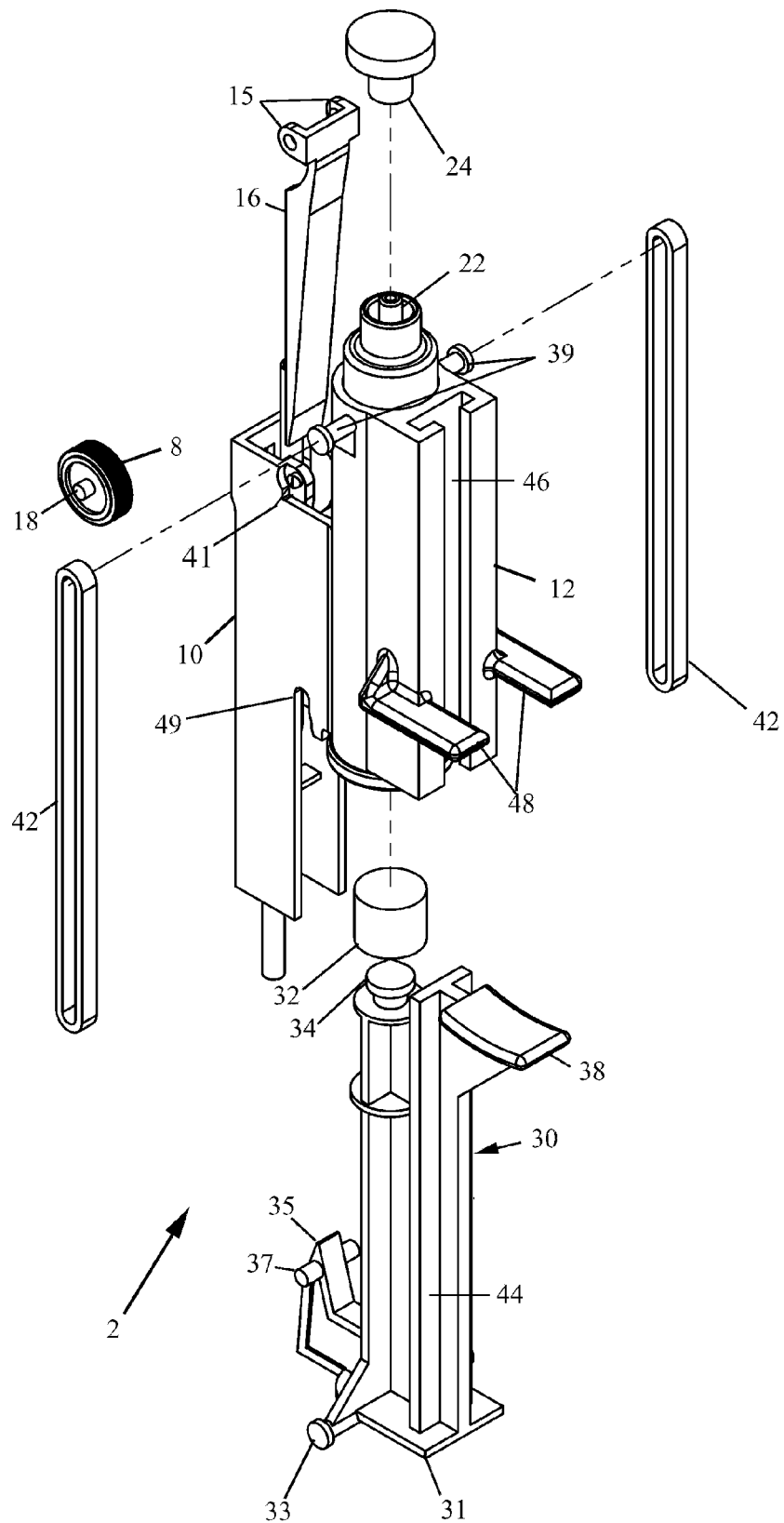
FIG. 2 is an exploded diagram of the regulator 2 as in FIG. 1.

FIG. 2 is an exploded diagram of the regulator 2 which shows that roller-clamp 8 comprises an annular hub with rubber tread mounted thereon, and opposing posts 18 forming an axle. These posts 18 of the roller-clamp 8 are carried in vertical notches 11 formed inside the trough of the main section 10, and the roller-clamp 8 is free to slide up and down along the notches 11 within the trough of the main section 10. In operation, the roller-clamp 8 variably constricts the IV tubing 4 to restrict flow.

A regulator back plate 16 is formed as an elongate ramp leading from a lower tip to a yoked mounting flange 15 at the top. The regulator back plate 16 extends downward through the trough of the main section 10 behind the roller-clamp 8, and is pivotally mounted therein by the yoked mounting flange 15 which fits within a recess formed at the top of the main section 10 and is pivotally held therein by outwardly protruding mounting pins 41 that extend out through holes in the yoked mounting flange 15. The regulator back plate 16 serves as a backing against which the roller-clamp 8 presses against to restrict flow. In the normally-closed position shown, the regulator back plate 16 bears against the IV tubing 4 and provides a backstop for normal operation of the roller-clamp 8 in the conventional manner of an IV roller-clamp, allowing thumb-adjustment of the flow rate from the forefront of the regulator 2. The more the roller-clamp 8 is thumb-rotated downward along aperture 14, the more pressure it applies against the IV tubing 4 and the more flow is restricted. Conversely, when rotated upwards, the roller-clamp 8 releases pressure on the IV tubing 4 and the flow is less restricted.

The plunger section 12 is defined by a central pressure chamber formed as a cylindrical cavity running up through the center. The pressure chamber leads upward to an upper outlet 22 (FIG. 2) with check valve 24 mounted there atop, and two opposed-protruding mounting posts 39 flanking the outlet 22. The check valve 24 only allows air to enter the pressure chamber in the plunger housing 12. A plunger 30 is slidably loaded into the pressure chamber, plunger 30 bearing an upper stopper 32 mounted atop a protruding post 34. The stopper 32 rides along the pressure chamber and seals it off. Plunger 30 further comprises an elongated plunger formed much like a syringe's, the plunger leading downward to a flat base 31, a pair of mounting posts 33 protruding outward on either side of the plunger near the base 31, and a forwardly/upwardly protruding wedge 35 likewise bearing a pair of opposed catch posts 37 at its tip. A pair of elastic bands 42 (one on each side) are each looped around one protruding post 39 on plunger housing 12 and downward around a corresponding mounting post 33 on that same side of the plunger near the base 31. The elastic bands 42 serve to bias the plunger 30 upward inside the plunger housing 12. The plunger 30 is slidably captured against the plunger housing 12 by a flange formed with opposing rails 44, the rails 44 slidably carried within a conforming channel 46 formed vertically along the plunger section 12. A thumb-depression tab 38 crops outward at the top of the rails 44 and this is used for manually depressing the entire plunger 30 downward out of the pressure chamber of plunger housing 12. Two opposing ears 48 are fixedly attached toward the bottom of the plunger housing 12 and protrude laterally outward, thereby providing a manual indexing for the thumb tab 38 and of the downward extent by which the plunger 30 is depressed. The two opposing ears 48 also allow the user to squeeze them together with the thumb tab 38.

Figure 3:
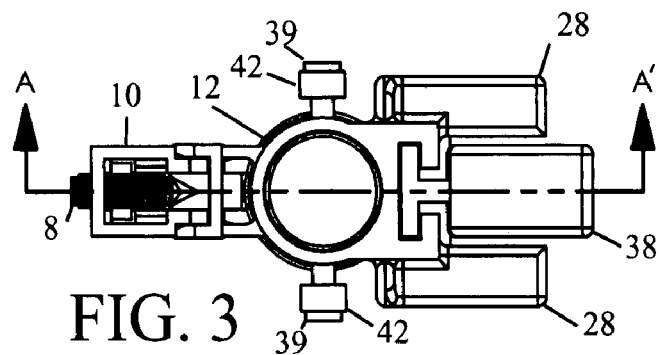
FIG. 3 is a top view of the regulator 2 of FIGS. 1-2.
Figure 4:
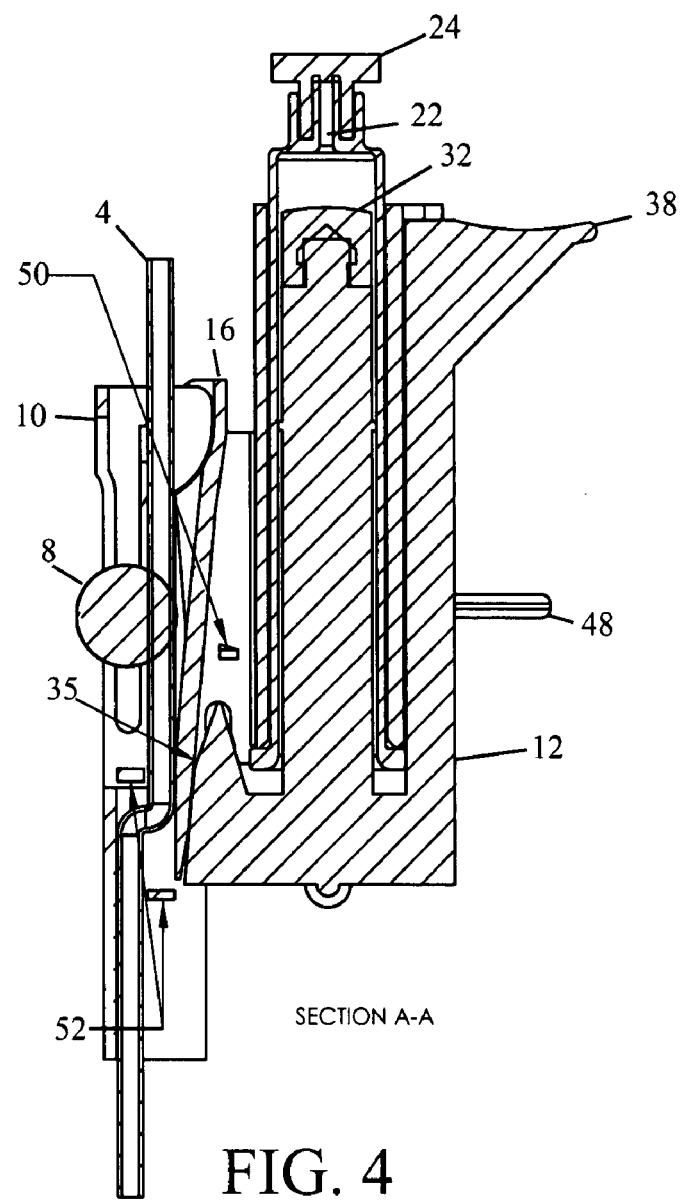
FIG. 4 is a cross-section of the regulator 2 taken along the lines A-A' of FIG. 3.

FIG. 3 is a top view of the regulator 2 of FIGS. 1-2, and FIG. 4 is a cross-section of the regulator 2 taken along the lines A-A' of FIG. 3. As best seen in FIG. 4, when in its normal (undepressed) plunger 30 position, the wedge 35 remains in contact with the regulator back plate 16 and biases it forward against the IV tube 4, sandwiching the tube 4 against the roller-clamp 8 and regulating IV flow.

In operation, when it is desirable to administer a bolus flush, a user depresses the thumb-depression tab 38 until limited by the opposing ears 48, thereby fully depressing the plunger 30 downward out of the pressure chamber of plunger housing 12. Air is freely inducted into the pressure chamber through the check valve 24. Eventually, the wedge 35 drops beneath the ramp of the regulator back plate 16 and frees it to swing backward, thereby releasing pressure on the IV tube 4 and allowing free flow.

In this plunger 30-down position the rubber bands 42 are fully extended and begin to bias the plunger upward within the pressure chamber. However, the pressure inside the pressure chamber resists this and the plunger 30 is only allowed to move slowly upward as air is slowly allowed to bleed out through the upper outlet 22. As the pressure chamber empties and plunger 30 moves slowly upward, the wedge 35 reencounters the regulator back plate 16 and again biases it forward against the IV tube 4, sandwiching the tube against the roller-clamp 8 and regulating further IV flow. The catch posts 37 formed on the wedge 35 of the plunger 30 eventually enter notches 49 formed in the side walls of the main section 10 and the plunger 30 thereby comes to rest.

Note also that backplate stops 50 formed as inwardly protruding tabs in the side walls of the main section 10 serve to restrict backward pivoting of the regulator back plate 16 and keep it from pivoting too far when the plunger is depressed, thereby ensuring that the wedge 35 will always slide properly in between the regulator back plate 16 and plunger 30 as seen in FIG. 4. Similarly, a lower series of protruding tabs 52 in the side walls of the main section 10 serve to maintain a crook in the IV tube 4 and prevents shifting around inside the main section 10.

The size of the pressure chamber, the outlet 22, and the resistance of the rubber bands may be determined empirically to produce a calibrated time delay during which the IV tube 4 permits a flushing free flow. To get an adequate flush volume, an adequate activation time is required and this is approximately 30 seconds of flush time. One of the advantages of the above-described regulator 2 is that it accomplishes a semi-automatic flush using components and a form factor that are similar to existing commercial roller regulators, thereby providing a familiar look and feel to doctors and nurses and encouraging widespread adoption. This also saves manufacturing cost. Moreover, by simply varying dimensions, the regulator 2 can be made compatible with most popular conventional brands and sizes of existing IV tubing sets.

Two additional embodiments are herein disclosed: a second that administers a flush for a specific period of time, and a third for a specific volume of flush solution.

Figure 5:
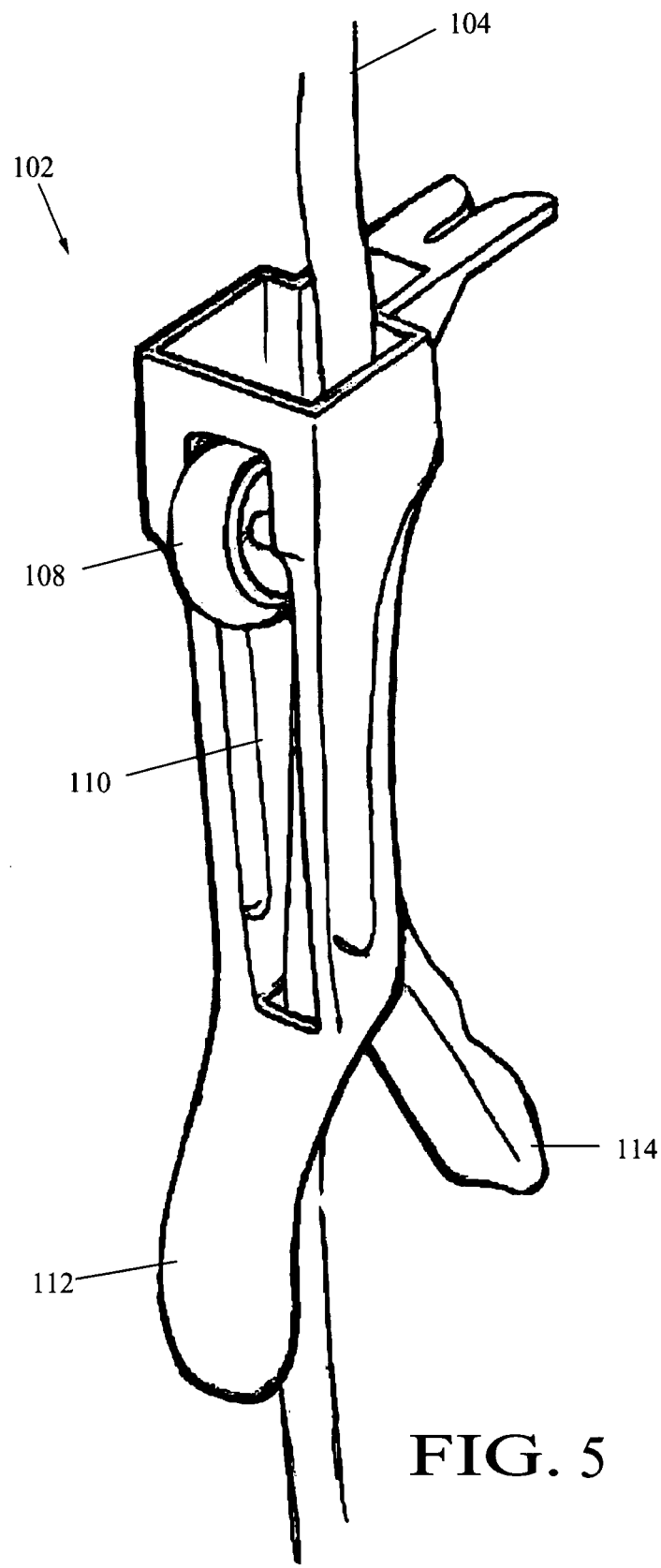
FIG. 5 is a perspective view of a regulator 102 for IV tubing according to a second embodiment that interrupts normal flow to flush for a specific period of time before returning to pre-flush flow.

FIG. 5 is a perspective view of a regulator 102 for IV tubing 104 according to a second embodiment that interrupts normal flow to flush for a specific period of time before returning to pre-flush flow. The regulator 102 generally comprises an elongated housing with main section 112 and compressible lever section 114 mounted pivotally thereon. The main section 112 is formed as a trough, and the existing IV tubing 4 runs through the trough of main section 112. A roller-clamp 108 is rotatably seated across the trough of the main section 112 and protrudes out of an aperture 110 in the front face of main section 112.

As best seen in the side cross-section of FIG. 6 and the front cross-section of FIG. 7, the IV tubing 104 runs internally through the main section over roller-clamp 108. While not explicitly shown, it is necessary to maintain a certain degree of friction between the roller-clamp 108 and the main housing section 112, and between the tubing 104 and the housing. Conventional rubber grommets may be used for this purpose. These will prevent the respective parts from sliding freely within the housing.

The compressible lever section 114 extends upward above its pivot point to a lever that bears against the IV tubing 104. The compressible lever section 114 is pivoted at a pin 117 that spans the trough of the main section 112. Both a compression spring 116 and a rotary damper 118 are mounted on the pin 117. The spring 116 biases the lower flange of the compressible lever section 114 away from the main section 112, maintaining a normally closed position. However, when the lower flange of the compressible lever section 114 is squeezed toward the main section 112, the rotary damper 118 then opposes the immediate closure of the lever 114 by the compression spring 116, and gradually reduces its counterbalancing force to provide a slow timed closure. In the normally-closed position the compressible lever section 114 bears against the IV tubing 104 and provides a backstop for normal operation of the roller-clamp 108, allowing thumb-adjustment of the flow rate from the front of the regulator 102. However, when it is desirable to administer a bolus flush, the compressible lever section 114 can be compressed manually against the main section 112, thereby lifting the backstop section of lever 114 away from the IV tubing, and opening the IV tubing 104 to full flow for a predetermined period of time.

Figure 8:
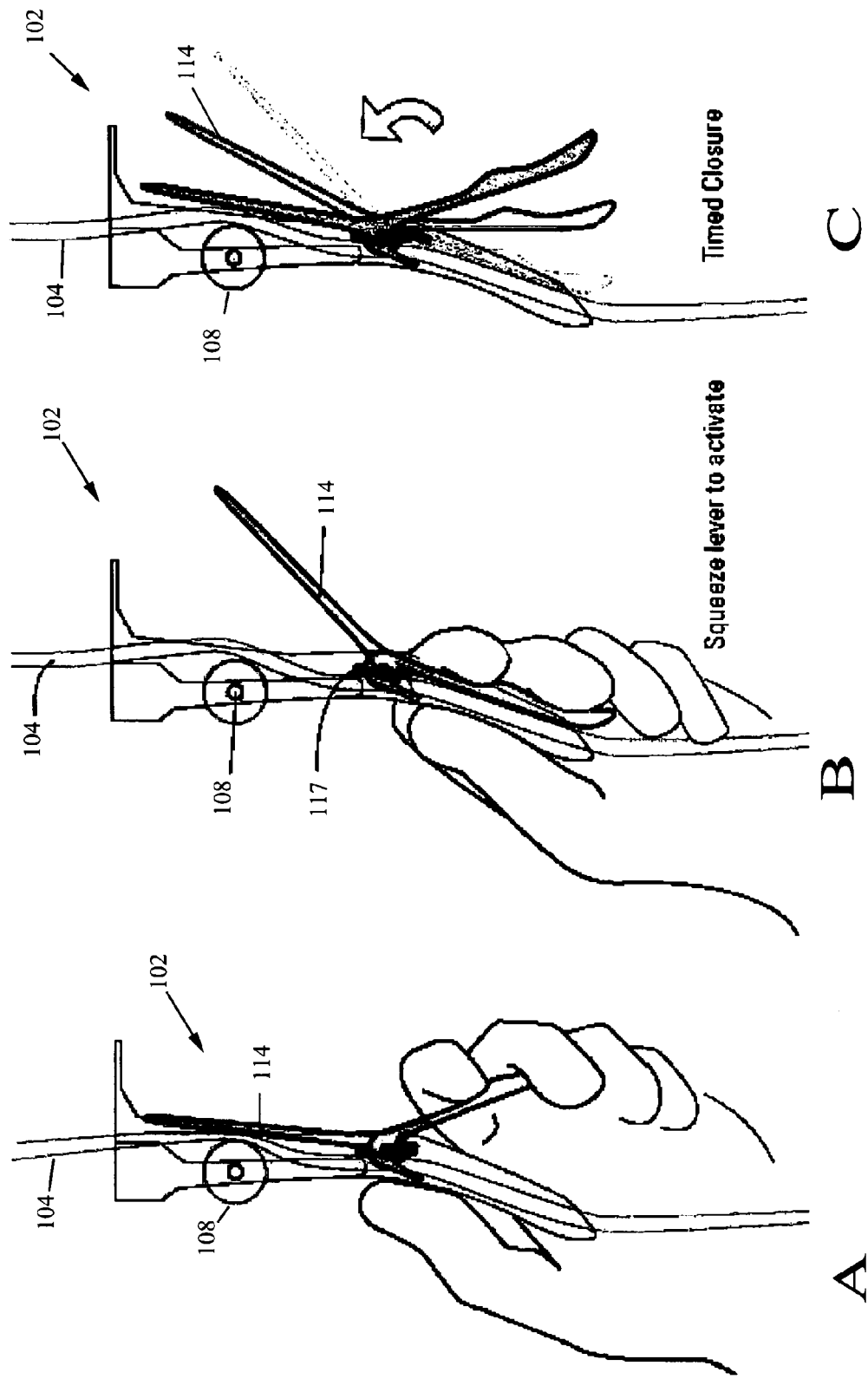
FIG. 8 (A-C) is a composite sequential illustration of the operation of the regulator 102.

This operation is shown in more detail in FIG. 8, which is a sequential illustration.

At FIG. 8(A) the regulator 102 is in the normally-closed position, with the upper flange of compressible lever section 114 bearing against the IV tube 104 and providing for normal operation of the roller-clamp 108, allowing thumb-adjustment of the flow rate from the front of the regulator 102.

At FIG. 8(B) the lower flange of the compressible lever section 114 has been squeezed against the main section 112, thereby lifting the backstop lever section away from the IV tube 104 and removing it as a backstop for normal operation. This fully opens the IV tubing 104 and initiates unobstructed fluid flow.

At FIG. 8(C) the compressible lever section 114 gradually returns to its original home position (under the spring bias of compression spring 116) to once again regulate fluid flow. This return home is effected over a calibrated time interval to limit the flush of FIG. 8(B) to a predetermined time.

The calibrated time interval is determined by the rotary damper 118, which initially counterbalances the compression spring 116 but gradually reduces its counterbalancing force, allowing the compression spring 116 to overcome it and return the compressible lever section 114 to its original home position. This returns to the configuration of FIG. 8(A) in which the compressible lever section 114 bears against the IV tube 104 and provides a backstop for normal flow-controlled operation.

Figure 9:
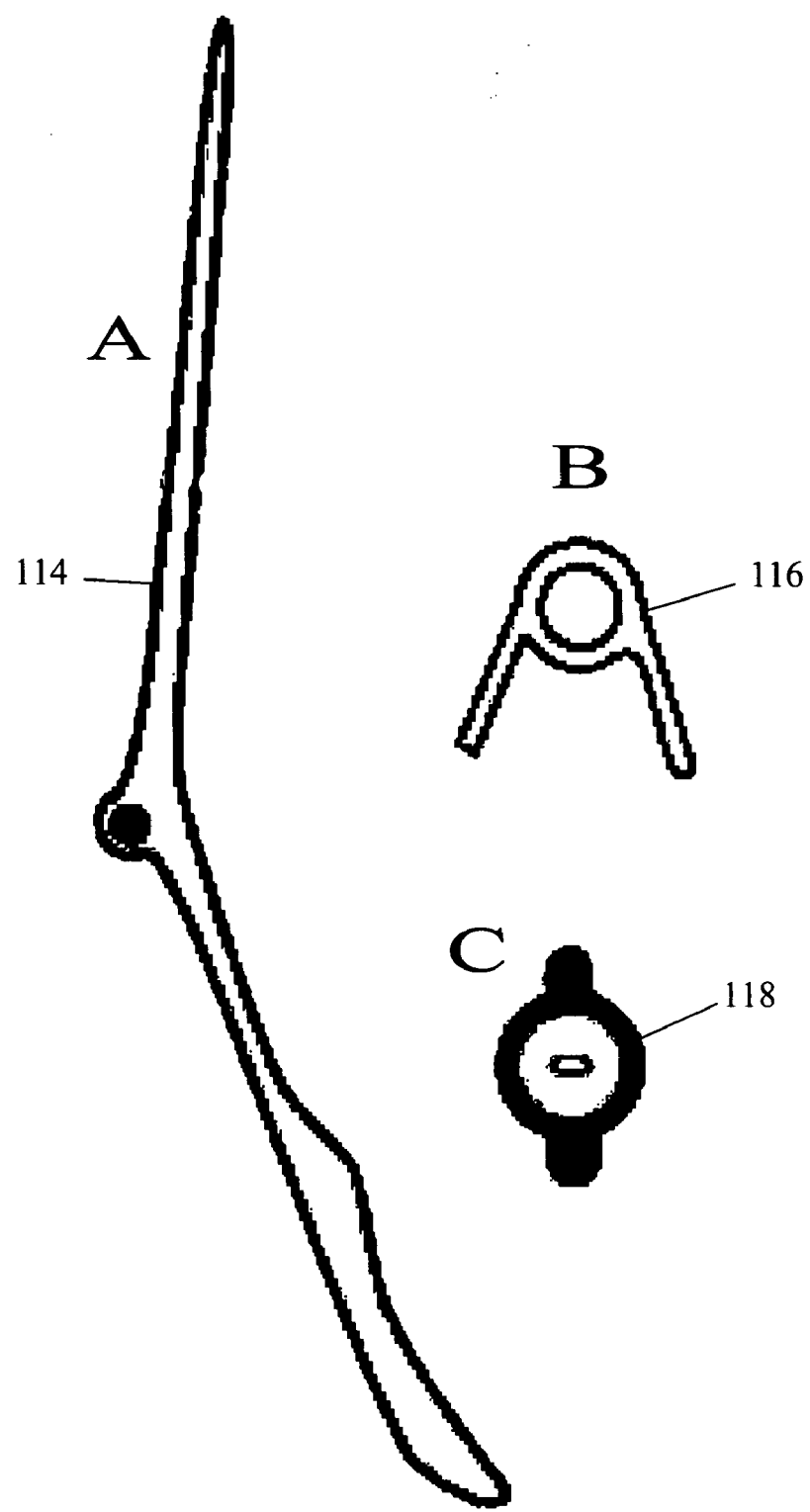
FIG. 9 (A-C) is a detailed view of the operative components of the regulator 102.

FIG. 9 shows the operative components of the regulator 102 including the lever 114 (at A), torsion spring 116 (at B) and rotary damper 118 (at C). The rotary damper 118 may be any small footprint rotary damper capable of generating enough braking torque to delay the full return of compression spring 116 by approximately thirty seconds. To get an adequate flush volume, an adequate activation time is required and this is approximately 30 seconds of flush time. There are a wide variety of commercially-available fluid-filled rotary dampers that will suffice. In actuality, the braking torque of any rotary damper will depend on the size of the surface of the rotor and housing disposed in contact with the viscous fluid. Thus, the torque increases when the dimensions of these elements are made larger. Nevertheless, it is possible to build a rotary damper small enough to conform to the footprint of a conventional IV roller-regulator such as shown and described in U.S. Pat. No. 5,497,863 to Schmidt et al. issued Mar. 12, 1996. Preferably, the rotary damper 118 used herein has an adjustable reverse-torque setting to provide regulator 102 with an adjustable activation time to allow the volume of fluid flushed to be varied. Nevertheless, the regulator 102 provides consistent activation times once the rotary damper 118 is set, within a specified repeatability tolerance. It is also noteworthy that the main housing 112 is formed with an enlarged frontal window 110 to allow rough visual inspection of the internal components and tubing 104. One of the advantages of the above-described regulator 102 is that it accomplishes a semi-automatic flush using components and a form factor that are similar to existing commercial roller regulators, thereby providing a familiar look and feel to doctors and nurses and encouraging widespread adoption. This also saves manufacturing cost. Moreover, by simply varying dimensions, the regulator 102 can be made compatible with most popular conventional brands and sizes of existing IV tubing sets.

FIGS. 10 and 11 are a front cross-section and side cross-section, respectively, of an alternate embodiment of the regulator 202 that administers a calibrated volume of bolus flush before return to a "pre-flush" flow setting, again eliminating the need to manually open and later reset the roller-clamp regulator or to administer a separate saline flush injection. This volume regulator 202 generally comprises an enclosed housing 224 with end-wise inlets for ingress of the plastic IV tubing 204 and opposing outlets for egress. The housing 224 may be plastic and is intended to enclose the internal components in a protected space. Two expandable/collapsible bladders 226A & 226B reside within the housing 224, preferably at the approximate midpoint and with ample room inside housing 224 to allow for expansion/contraction. One wall of each bladder 226A & 226B may be affixed to a sidewall of the housing 224 by a grommet 227 or the like, provided that the grommets 227 effect a fluid tight seal. However, grommets 227 are not necessary as the bladders 226A & 226B can hang freely inside the housing 224 since they are substantially anchored at the top and bottom by the tubing 204.

The housing 224 may be elliptical in shape although other geometries are possible. An elliptical shape presents a relatively smooth inner profile and minimize cross sectional area when inline with the tubing 204. The housing 224 is preferably formed of clear plastic to allow an operator to see the internal tubing 204 and bladders 226A & 226B. The bladders 226A & 226B may be formed of siliconized rubber or more conventional IV bag material (EVA, PVC, PP) or other like materials, and are preferably tinted two different colors so that the operator can also see which one is distended. The bladders 226A & 226B are size and elasticity-calibrated to expand to predetermined volumes in the range of 5 to 10 milliliters (ml). The bladders 226A & 226B are each coupled at both ends to plastic IV tubing 204, such that dual IV tubes 204 enter the inlet at the top of the housing 224 (or a single tube 204 enters and bifurcates to both bladders 226A or 226B). Likewise, dual IV tubes 204 branch from the respective bladders 226A & 226B and leave the bottom of the housing 224 (or a pair of IV tubes 204 branch from the respective bladders 226A and 226B and conjoin to a single tube 204 leaving the outlet at the bottom of housing 224). Any bifurcation and joining of tubes 204 may occur inside or outside the housing 224. The tubing 204 is preferably made of relatively large bore IV tubing to allow for the rapid inflow and outflow of fluid from the bladders 226A & 226B. A pair of rubberized tube holders 228 are situated at the top and bottom of housing 224 near the inlets and outlets to capture the tubing 204 therein without constricting fluid flow. The housing 224 is further formed with two channels 222 (top) and 223 (bottom) defined along the inner surface of the housing 224. These channels 222 and 223 are formed as shallow concavities and serve to contain the tubing 204 as well as providing a directional guide for expansion of the bladders 226A & 226B.

As best seen in FIG. 11, a slider paddle 230 is pivotally mounted midway along the housing 224 at a pivot joint 231. The slider paddle 230 comprises an elongated toggle member having an arcuate upper yoke 232 and arcuate lower yoke 234, both yokes being uniformly offset to engage the tubing 204 immediately adjacent to the tubing holders 228. The upper yoke 232 and lower yoke 234 both embrace the bifurcated tubing 204 at the respective positions. In general operation, the slider paddle 230 may be pivoted so that the upper yoke 232 constricts one tube and opens the other, while the lower yoke 234 does the same. This effectively opens the fluid flow path into one bladder (e.g., 226A) while closing the output (to allow that bladder 226A to fill) while closing flow into the other bladder 226B and opening the output (to allow that bladder 226B to drain). Conversely, the slider paddle 230 may be pivoted in the opposite direction so that the upper yoke 232 releases the constricted tube and closes the open tube, the lower yoke 234 doing the same. This changes the fluid flow path, allowing the previously filled bladder 226A to drain and the previously draining bladder 226B to fill. In effect, the slider paddle 230 works like a toggle switch by lever action to selectively fill one bladder 226A while draining the other 226B, and vice versa.

Figure 12:
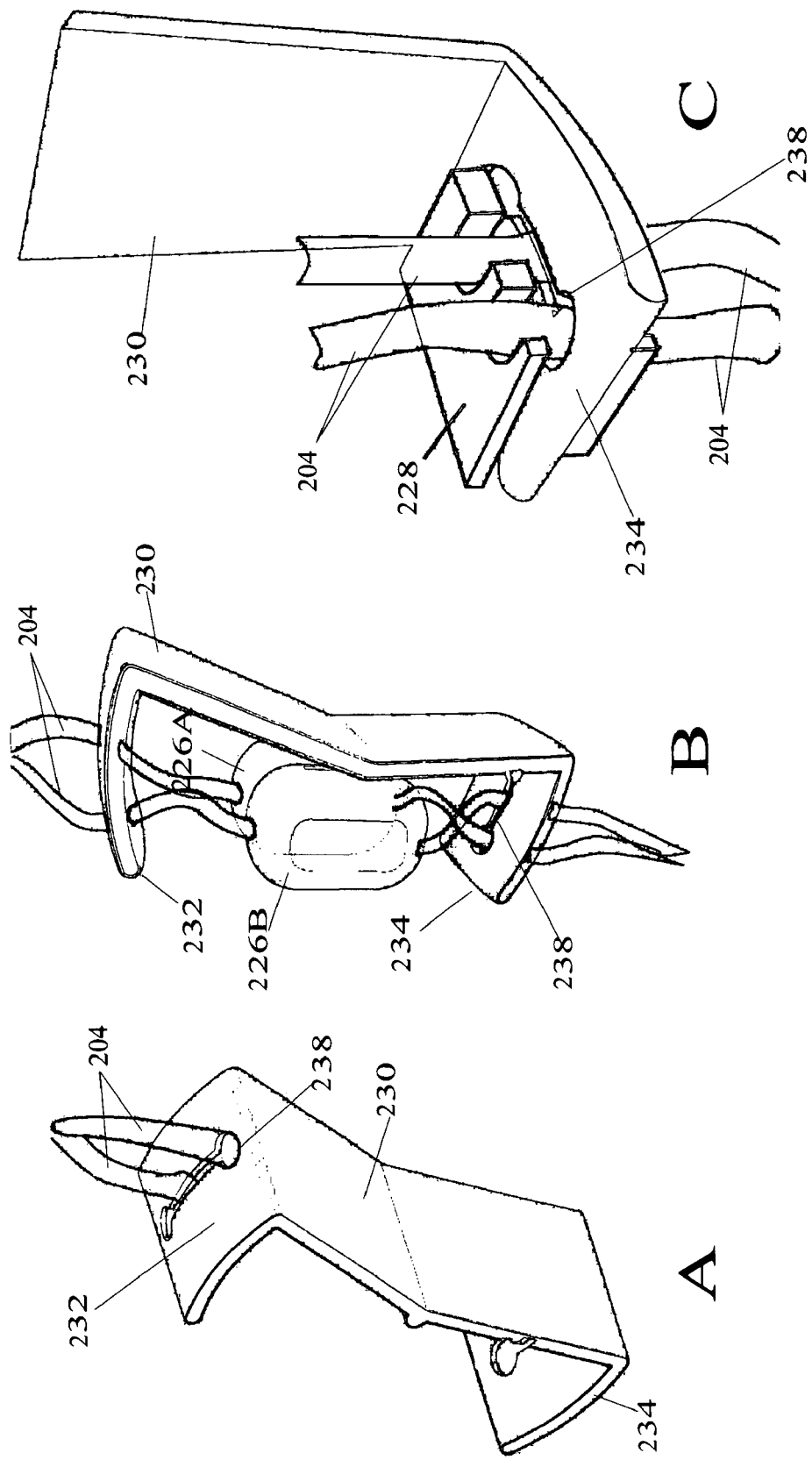
FIG. 12 (A-C) is a composite view with enlarged illustrations of the slider paddle 230 and internal tube 204 configuration of the regulator 202 of FIGS. 10-11.

FIG. 12 is a composite view with enlarged illustrations of the slider paddle 230 and internal tube 204 configuration. As seen at FIG. 12A, the upper yoke 232 of slider paddle 230 is formed with a groove 238 comprising opposing (offset) apertures connected by a constricted slot. The IV tubes 204 pass down through the groove 238 and, if positioned in an aperture, remain open but if moved into the slot will be closed. Thus, in one position of slider paddle 230 one tube 204 will pass through an aperture and remain open, while the other is engaged in the slot and is closed. Conversely, if the slider paddle 230 is pivoted, the tubes 204 will switch, the closed one moving into an aperture and becoming open, while the other moving into the slot and closing.

As seen in FIG. 12C the lower yoke 234 of slider paddle 230 is formed with an identical groove 238 with opposing (offset) apertures connected by a constricted slot. Similarly, the IV tubes 204 from the bladders 226A & 226B pass down through this groove 238 and, if positioned in an apertures, remain open but if moved into the slot will be closed. Thus, in one position of slider paddle 230 one tube 204 will pass through an aperture and remain open, while the other is engaged in the slot and is closed. If the slider paddle 230 is pivoted, the closed tube 204 opens and the open tube 204 closes.

As seen in FIG. 12B, the tubes 204 are twisted to form a cross-over. This ensures that in one position of slider paddle 230 one bladder 226A has an open input and closed output (to fill), while the other bladder 226B has a closed input and open output (to drain), the converse occurring for the other position of slider paddle 230.

Figure 13:
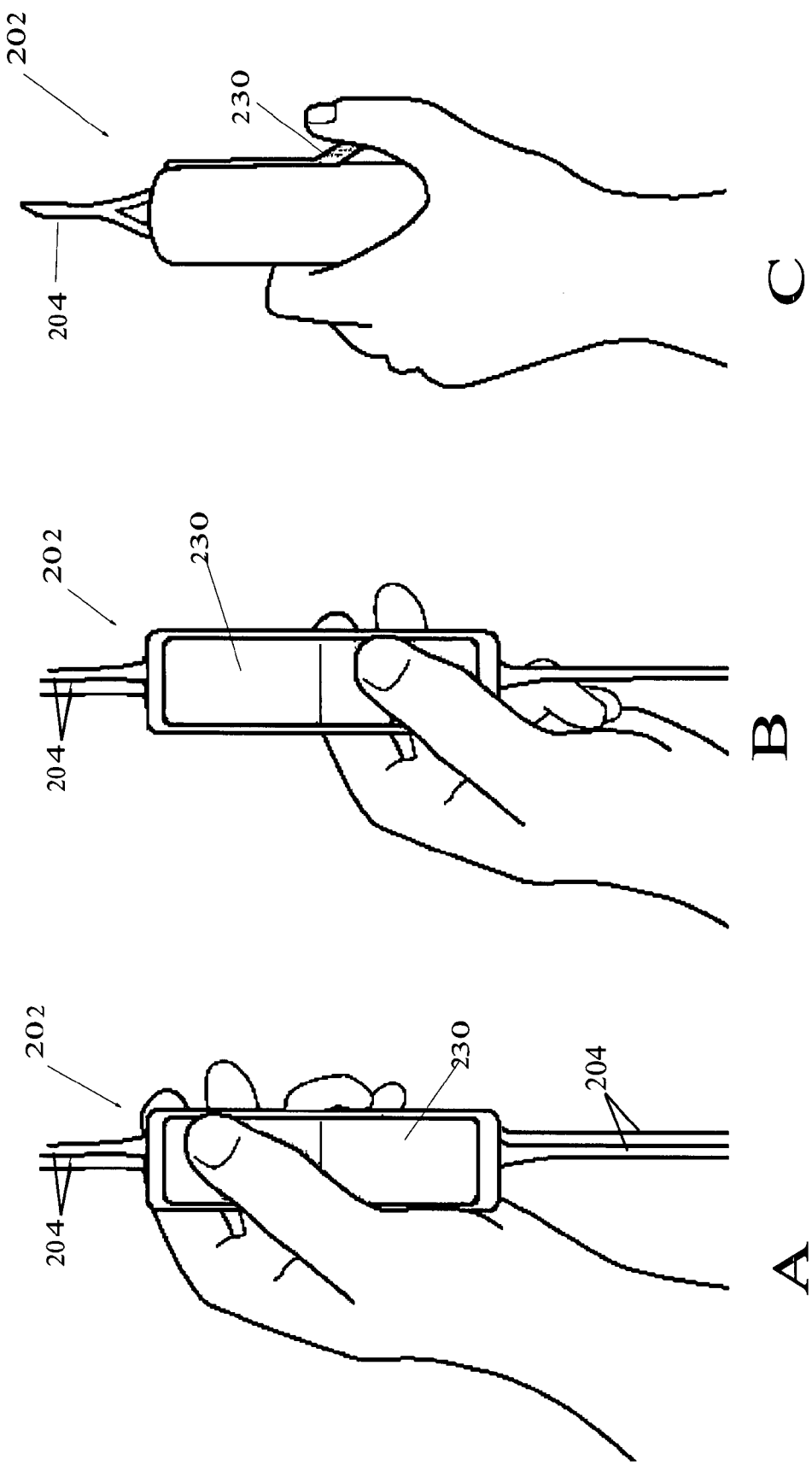
FIG. 13 (A-C) is a composite sequential illustration of the operation of the volume regulator 202 of FIGS. 10-12.
Figure 14:
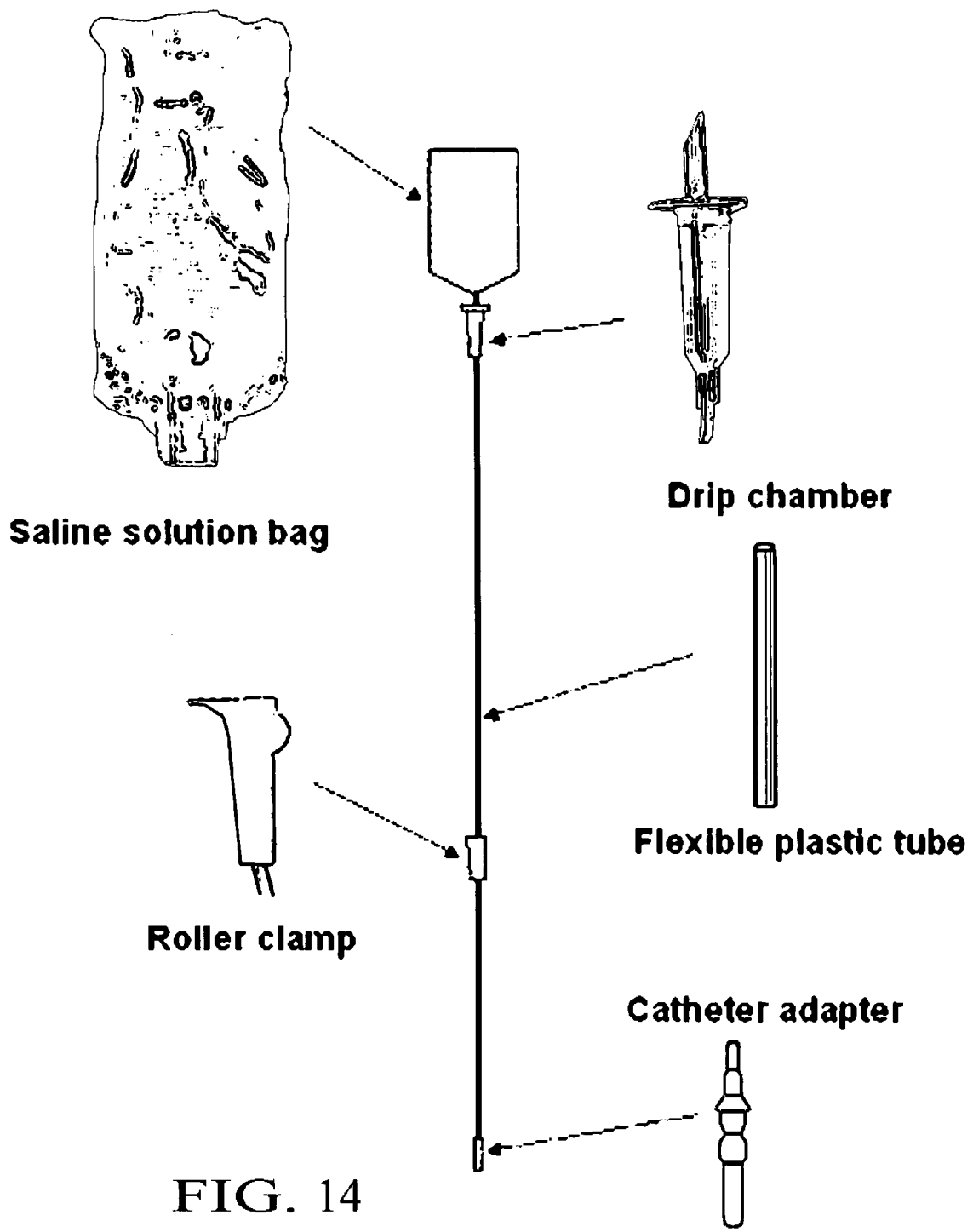
FIG. 14 is a perspective view of a conventional IV administration set.

The details of operation are more apparent in FIG. 13 which is a composite sequential view of the volume regulator 202. Intravenous fluid is fed into the device by gravity from a conventional IV bag (not shown). Initially the slider paddle 230 is in one position as seen at (A), and consequently one tube 204 entering from the top is open to receive fluid into one bladder 226A (obscured) while the other input tubing 204 is closed and pinched by the upper yoke 232 of slider paddle 230. This allows one bladder to fill and expand into the elliptical space inside housing 224. Since the tubing 204 to the other bladder is closed only one bladder is filling or full at any given time. The other is emptying or empty, and the draining bladder is flushing fluid into the distal output tubing 204. Approximating the bladders 226A & 226B as cylinders, a volume of 10 ml would necessitate bladders 226A and 226B of approximately of 1 cm radius and 3.3 cm height. The cross-over tubing 204 arrangement described above ensures that one bladder fills while the other drains. Regular flow is not maintained through either bladder since the bladders 226A & 226B can only be emptying completely or filling completely. Medications must only be given distal to the device, such that it is not possible for them to become entrained within the bladders—thereby leading to unpredictable administration into the bloodstream.

By simply moving the slider paddle 230 back and forth as needed, the operator has a predetermined volume of fluid that flushes the tubing 204. The bladder, when empty, collapses on itself with its walls now apposed.

The above-described regulator 202 may also be used in conjunction with a conventional roller-clamp as described previously to regulate fluid, and one skilled in the art should readily recognize that a roller-clamp mechanism may be incorporated inside housing 224 if desired to merge the devices for this purpose. Moreover, the slider paddle 230 may be color-coded similar to the bladders 226A & 226B to correlate the two positions of the slider paddle with the two bladders 226A & 226B.

It should now be apparent that all three of the above-described embodiments 2, 102, 202 allow interruption of normal controlled-flow for a safe and convenient bolus flush (full flow of IV fluid), regulators 2 and 102 for a specific period of time, and regulator 202 for a specific volume of saline flush, before returning to a "pre-flush", regulated flow setting. This simplifies the process of administering a bolus medication followed by saline flush, improves safety and eliminates over flushing.

Having now fully set forth the preferred embodiments and certain modifications of the concept underlying the present invention, various other embodiments as well as certain variations and modifications thereto may obviously occur to those skilled in the art upon becoming familiar with the underlying concept. It is to be understood, therefore, that the invention may be practiced otherwise than as specifically set forth herein.

We claim:
1. A flow regulator for IV tubing, comprising:
a housing having an IV tube running through it;
a roller-wheel carried within said housing on a first side of said IV tube and adjustable therein to impart a controlled bias against said IV tube, thereby selectively adjusting fluid flow through said IV tubing;
an elongate pressure plate pivotally mounted in said housing on a second side of said IV tubing opposed to said first side, said pressure plate pivotable between a fixed first position in which it bears on said IV tube to provide a backing against the bias of said roller-wheel, and a second position in which said IV tube is released from the bias imparted by said roller-wheel; and
a manual actuator mounted to said housing and engaged to said pressure plate, said manual actuator comprising
a depressible member movable from a normally-closed position to an open position, said depressible member having a protruding release member disposed to engaged said pressure plate , and
a sustained return mechanism engaged to said depressible member for gradually returning said depressible member to said normally-closed position, and said protruding release member engaging said pressure plate to maintain it in said fixed first position when said depressible member is in said normally-closed position, and releasing said pressure plate to pivot into said second position when said depressible member is in said open position, thereby temporarily administering a bolus flush.

2. The flow regulator according to claim 1, wherein said manual actuator administers a bolus flush for a predetermined period of time.

3. The flow regulator according to claim 1, wherein said manual actuator administers a pre-determined volume of bolus flush.

4. The flow regulator according to claim 2, wherein said manual actuator further comprises a pneumatic cylinder.

5. The flow regulator according to claim 4, wherein said pneumatic cylinder is counter-opposed by said return mechanism.

6. The flow regulator according to claim 5, wherein said return mechanism comprises at least one elastic band.

7. The flow regulator according to claim 2, wherein said manual actuator comprises a plunger slidably mounted in a chamber and under bias to a home position, a one way valve for allowing air into said chamber, a bleed outlet for allowing air to slowly escape said chamber, and at least one thumb tab for allowing a user to slide said plunger to a second position in which said chamber is filled with air.

8. A flow regulator for IV tubing, comprising:
a housing having an IV tube running through it;
a roller-clamp seated in said housing and accessible there from, said roller-clamp having a wheel and a backplate, said wheel engaged to said tubing and adjustably positioned a distance from said backplate to selectively adjust fluid flow through said IV tubing by compressing said tubing against said backplate; and
a manual actuator mounted to said housing and engaged to said roller-clamp for selectively disengaging said wheel from said IV tubing to administer a bolus flush by increasing said distance, said actuator further comprising
a plunger slidably mounted in a chamber and maintained under bias toward a home position,
a one way valve for allowing air into said chamber,
a bleed outlet for allowing air to slowly escape said chamber, and
at least one thumb tab for allowing a user to slide said plunger to a second position in which said chamber is filled with air.

* * * * *